United States Patent
Wagner et al.

(10) Patent No.: US 7,173,075 B2
(45) Date of Patent: Feb. 6, 2007

(54) GAS RELEASING SEALING AND FILLING COMPOSITIONS

(75) Inventors: Jeff A. Wagner, Salt Lake City, UT (US); Neil T. Jessop, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 288 days.

(21) Appl. No.: 10/929,296

(22) Filed: Aug. 30, 2004

(65) Prior Publication Data

US 2006/0047012 A1    Mar. 2, 2006

(51) Int. Cl.
*A61K 6/083*     (2006.01)
*C08K 3/22*      (2006.01)
*C08K 3/36*      (2006.01)
*C08K 5/23*      (2006.01)

(52) U.S. Cl. ............... 523/116; 523/118; 524/190; 524/431; 524/451; 524/493; 433/228.1

(58) Field of Classification Search ........... 523/116; 524/190; 433/228.1
See application file for complete search history.

(56) References Cited

U.S. PATENT DOCUMENTS

| | | | |
|---|---|---|---|
| 4,110,184 A | 8/1978 | Dart et al. | 204/159.23 |
| 4,362,842 A | 12/1982 | Masuhara et al. | 524/854 |
| 4,433,958 A | 2/1984 | Fellman et al. | 433/199 |
| 4,491,453 A | 1/1985 | Koblitz et al. | 433/217 |
| 4,552,906 A | 11/1985 | Podszun et al. | 523/115 |
| 4,772,031 A * | 9/1988 | Poppo | 277/316 |
| 5,002,475 A | 3/1991 | Graefe | 425/135 |
| 5,380,772 A | 1/1995 | Hasegawa et al. | 522/14 |
| 5,834,532 A | 11/1998 | Yamamoto et al. | 523/118 |
| 5,877,232 A | 3/1999 | Storch et al. | 523/116 |
| 6,184,339 B1 | 2/2001 | Stansbury et al. | 528/407 |
| 6,353,041 B1 | 3/2002 | Qian | 523/116 |
| 6,455,608 B1 | 9/2002 | Jia et al. | 523/115 |
| 6,500,004 B2 | 12/2002 | Jensen et al. | 433/228.1 |
| 6,506,815 B2 | 1/2003 | Shinozaki et al. | 522/74 |
| 6,620,232 B1 | 9/2003 | Kraft et al. | 106/404 |
| 2002/0016420 A1 | 2/2002 | Zarnoch et al. | 525/418 |
| 2003/0153645 A1 | 8/2003 | Sun et al. | 523/116 |
| 2003/0225182 A1 | 12/2003 | Walz et al. | 523/116 |

FOREIGN PATENT DOCUMENTS

| | | | |
|---|---|---|---|
| EP | 0209700 | 8/1990 | |
| GB | 1113722 | 5/1968 | |
| JP | 62132904 | 6/1987 | |
| JP | 62177001 | 8/1987 | |
| JP | 3130211 | 6/1991 | |
| JP | 4335008 | 11/1992 | |
| JP | 8188516 | 7/1996 | |
| JP | 9100208 | 4/1997 | |
| JP | 2002/338422 | 11/2002 | |
| WO | WO 0153413 | 7/2001 | 6/67 |

OTHER PUBLICATIONS

Fujisawa, S., "Effect of Phenolic Compounds on the Polymerization of Methyl Methacrylate" Dent Master, 8(5): 324-6 1993.
Kadoma Y, et al., "Kinetic Evaluation of Reactivity of Bisphonol A Derivatives as Radical Scavengers for methacrylate Polymerization" Biomaterials, 21(21): 2125-30 2000.
"Vazo® Water Soluble Grades" DuPont Specialty Chemicals, Technical Information Feb. 1999.
Silwet L-77 Surfactant, Setre Chemical Company, Material Safety Data Sheet, 1998.

* cited by examiner

*Primary Examiner*—Tae H Yoon
(74) *Attorney, Agent, or Firm*—Workman Nydegger

(57) ABSTRACT

Sealing and filling compositions for use in filling and/or sealing a root canal. The sealer and filler compositions include a polymerizable material that shrinks when polymerized. The composition also includes a gas releasing component that at least partially offsets the shrinkage caused by polymerization of the polymerizable material. The gas releasing component offsets polymerization shrinkage by creating tiny gas bubbles in the polymeric material, which causes expansion. The gas releasing component can be an acid and a base such as citric acid and sodium bicarbonate, which when mixed give off carbon dioxide. The composition can also include a dispersing agent to disperse the gas bubbles throughout the composition.

26 Claims, No Drawings

GAS RELEASING SEALING AND FILLING COMPOSITIONS

BACKGROUND OF THE INVENTION

1. The Field of the Invention

The present invention relates to compositions used in dentistry for sealing and/or filling a dental preparation. In particular, embodiments of the present invention relate to sealing and filling compositions that release a gas internally to offset the effects of shrinkage that occurs during polymerization.

2. The Relevant Technology

Resins are frequently used in dentistry and other fields as sealers and fillers. Recent developments in resin technologies have produced very strong resins with superior bonding properties.

Resins are useful sealants because they can be made non porous with strong bonding characteristics. The ability to resist permeation prevents bacteria and other foreign matter from contaminating the underlying tissue.

Resins are good fillers because they are easily shaped, bond well, and are very hard and durable. Resins are typically fluid when applied to a material. Because the resin is initially fluid, it can take the shape of a void, e.g., a cavity or dental preparation in a tooth. Yet after the resin is polymerized it is very hard and durable and bonds well to the surrounding tissue.

One disadvantage of conventional resins is that they typically undergo shrinkage when they polymerize (i.e., harden). During polymerization, the polymeric monomers are chemically bonded, thereby becoming more ordered and capable of packing more closely together. A more ordered configuration generally decreases the volume of the polymeric material. The volume reduction experienced during polymerization is known as "polymerization shrinkage".

Many attempts have been made to reduce or eliminate polymerization shrinkage. One common technique involves adding fillers to the composition. Because the filler does not undergo polymerization, the filler does not contribute to shrinkage. Thus, as the percentage of polymer in the composition is reduced, the overall shrinkage of the composition is proportionately reduced. Although adding fillers can reduce the amount of shrinkage, fillers alone cannot eliminate shrinkage because some amount of polymer will always be required. Furthermore, the amount of filler that can be included may be limited by required or desired performance properties in the final composite.

Others have attempted to counteract polymerization shrinkage by using particular monomers that undergo little or no shrinkage, or even experience expansion, during polymerization. For example, some prior art resins use cyclic monomers to carryout polymerization. In this case, ring opening increases the volume of the resin and offsets the shrinkage that occurs in the polymerization step.

While these compounds can reduce shrinkage, their use is very limited. First, the final properties of the composite depend on the monomers used to create the polymeric material. Therefore, when a particular monomer is used for its non-shrinking characteristics, it will also impart inherent characteristics in the final product. Moreover, because of the limited number of non-shrinking polymers that are available, the range of possible characteristics and properties are likewise limited. This technique of reducing polymerization shrinkage cannot be used with the many existing resins that have been developed to perform under specific conditions and for specific purposes. Furthermore, it would require coincidental circumstances to find a polymer for which polymerization shrinkage could be optimized that would result in optimal material properties.

While some techniques, such as using a filler or utilizing low shrinkage polymers, have minimized polymerization shrinkage, there exists a great need to further reduce polymerization shrinkage or completely offset its effects. Even small amounts of shrinkage can negatively affect resin performance. This is particularly true for certain applications such as dental sealers and fillers.

For example, following an endodontic root canal procedure, in which the root canal is cleaned using special root canal tools and irrigation devices, it is important to fill and seal the evacuated root canal to preserve the dead tooth from further decay that might compromise the integrity of the tooth and cause infection. In a typical procedure, one or more soft, resilient, needle-like inserts known as "gutta percha" points are inserted in each root canal branch in order to at least partially seal and fill the root canal.

Conventional techniques require multiple gutta percha cones per canal and laborious "later condensation" techniques. For some, it requires heating the gutta percha in an attempt to make it flow into the lateral canals. However, this technique, coupled with the generally hydrophilic properties of gutta percha, make it hard to achieve fine adaptation to canal walls and flow into the dentinal tubules.

Resins in conjunction with gutta percha and antiseptic pastes have been used to fill and seal root canals following a root canal procedure. The composite resins provide a beneficial technique for filling and sealing a root canal because the resin can be inserted into the root canal in a fluid form and then hardened by polymerization in a curing step. The resins can also be designed to have a desired hardness and adhesiveness to the root canal wall to create a good seal.

Unfortunately, polymerization shrinkage has the potential of disrupting bonding between the sealer and the root canal wall, tooth, or other material. As the resin undergoes shrinkage during polymerization, the composite can pull away from the tooth material and break the seal or weaken the bond between the two. Even small gaps created in this manner can be problematic since bacteria can enter and cause decay or infestation.

Therefore, what is needed are dental filling and sealing compositions that are able to at least partially offset or eliminate the effects of polymerization shrinkage.

BRIEF SUMMARY OF THE INVENTION

Exemplary embodiments of the present invention overcome the foregoing problems in the prior art by providing filling and sealing compositions that undergo little or no polymerization shrinkage. In one embodiment, the composition includes a polymerizable material that shrinks as it is polymerized to form a polymer. To offset such shrinkage, the composition also includes a gas-releasing component mixed with the polymerizable material. During polymerization, the gas releasing component releases a gas that causes the volume of the composition to expand. The expansion of the composition due to gas formation counteracts the polymerization shrinkage caused by the polymerizable material.

In an exemplary embodiment, the composition also includes a polymerization initiator. The initiator is configured to cause the polymerizable material harden or cure. In the case of a chemical initiator, the composition is preferably a multipart composition such that the polymerizable material and polymerization initiator do not come in contact until polymerization is desired.

The gas releasing component can also be separated into multiple parts that are mixed upon initiation. In one embodiment, the gas component includes an acid, such as citric acid, and a base, such as sodium bicarbonate. The acid and base are kept in separate parts until polymerization is initiated, at which time the acid, base, polymerizable material, and initiator are combined. The acid and base react to produce a gas such as $CO_2$, for example, which causes sufficient expansion to offset polymerization shrinkage.

In an exemplary embodiment, the duration of polymerization and duration of gas production are controlled to properly expand the composition. The rate of polymerization is controlled by increasing or decreasing the amount of initiator. Gas production on the other had is controlled by the concentration of acid and base. In an exemplary embodiment, gas production continues during polymerization until the composition's volume becomes fixed and rigid due to polymerization and hardening. In yet a further embodiment, the composition of the present invention includes a dispersing agent to disperse the gas within the composition.

Embodiments of the present invention provide significant advantages over known sealer and filler compositions because the compositions of the present invention can be configured to have little or no shrinkage. By producing sufficient gas during polymerization, small bubbles form in the composition, thereby increasing the volume of the composition so as to offset polymerization shrinkage.

The little or no shrinkage of the filling and sealing compositions of the present invention allows the composition to seal much better to dental tissue such as a root canal wall. The improved sealing prevents bacteria and other contaminates from reaching the underlying tissue.

The sealing and filling compositions of the present invention are able to seal, even though bubbles form in the composition. By adding a dispersing agent, the bubbles are so finely dispersed that they do not interconnect. The bubbles are isolated (i.e., closed celled) such that there is no path through which bacteria or contaminants can pass through to the underlying tissue. Furthermore, the finely dispersed bubbles do not significantly compromise the structural integrity and strength of the cured composition.

Because the gas-producing mechanism can be carried out independent of the polymerization step, the anti-shrinkage mechanism of the present invention can be used with most resin compositions. Furthermore, the gas production can be optimized independent of the nature of the polymerization reaction. This allows polymerization to be optimized as well as reduction in shrinkage.

The present invention is also versatile with respect to the type of gas releasing component. The gas releasing component can be select to be compatible with most any polymerizable material. For instance if a particular resin is not compatible with acids and bases, a different gas releasing component such as azo-bis-isobutyronitrile can be used. Furthermore, the invention is not limited to compositions initiated by a chemical initiator. In another embodiment, a photoinitiator may be used to instigate polymerization. In this embodiment, the photoinitiator or a chemical initiator or a mixture of chemicals such as acid and bases can be used to release a gas into the composition.

These and other features of the present invention will become more fully apparent from the following description and appended claims.

DETAILED DESCRIPTION OF EXEMPLARY EMBODIMENTS

Exemplary embodiments of the present invention relate to polymerizable resins used to fill and/or seal a void, such as a root canal or other dental preparation. The filler composition includes a polymerizable material that normally shrinks upon polymerization, but that also includes a gas releasing component that at least partially offsets the polymerization shrinkage.

I. Polymerizable Materials

A. Polymerizable Resins

The sealing and filling compositions according to the present invention include at least one polymerizable resin material. The polymerizable resin is initially in a liquid or shapeable form. As discussed below, the polymerizable resin is cured to form a polymerized material. The polymerizable resins used in the present invention, like most polymerizable resins, shrink upon polymerization.

Examples of suitable primary polymerizable resins include a wide range of acrylates, methacrylates, alkylhydroxy methacrylates, alkylamino methacrylates, and derivatives thereof. More specific examples of polymerizable materials include glycidyl dimethacrylate, 2-hydroxy ethyl methacrylate, 3-hydroxy propyl methacrylate, 4-hydroxy butyl methacrylate, triethylene glycol dimethacrylate, and polyethylene glycol dimethacrylate.

In one exemplary embodiment, the polymerizable resin is an oxyphosphorus alkyl methacrylate, such as bis glycerol dimethacrylate phosphate. Examples of other oxyphosphorus alkyl methacrylates within the scope of the invention include bis 2-hydroxy ethyl methacrylate phosphate, phosphate ester of p-hydroxyphenyl methacrylamide, phosphate ester of 3-hydroxy propyl methacrylate, and phosphate ester of 4-hydroxy butyl methacrylate. The oxyphosphorus group increases the adhesiveness and water solubility (i.e. hydrophilicity) of the resulting resin. As discussed more fully below, controlling water in the resin can be import for certain gas releasing components such as an acid-base reaction. Oxyphosphorus polymerizable materials are suitable for use with gas releasing components that require water.

One or more additional (or diluent) monomers can be added to achieve the desired properties of initial flowability, curability, and final cured strength and hardness. Diluent monomer suitable for use in the present invention include urethane dimethacrylate, p-hydroxyphenyl methacrylamide, butane diol dimethacrylate, and bisphenol-A-diglycidyl dimethacrylate ("Bis-GMA").

The primary polymerizable resins are preferably included in a concentration ranging from about 1% to about 90% by weight of the composition, more preferably from about 10% to about 80% by weight, and most preferably from about 20% to about 70% by weight of the composition.

The diluent monomers may be included in amounts of up to about 95% by weight of the composition, preferably in a range from about 10% to about 80%, and more preferably in a range from about 30% to about 70% by weight of the composition.

B. Initiators

Initiators are provided in the composition to induce polymerization of the polymerizable material. The initiators or curing agents may include radiant energy polymerization initiators with or without an appropriate organic amine additive or a chemical initiator with an appropriate organic amine additive.

1. Photoinitiators

Examples of photoinitiators within the scope of the invention include camphor quinone, benzoin methyl ether, 2-hydroxy-2-methyl-1-phenyl-1-propanone, diphenyl 2,4,6-trimethylbenzoyl phosphine oxide, benzoin ethyl ether, benzophenone, 9,10-anthraquinone, and derivatives thereof.

Photoinitiators are preferably included in an amount in a range from about 0.05% to about 5% by weight of the composition, more preferably in a range from about 0.1% to about 2% by weight, and most preferably in a range from about 0.2% to about 1% by weight of the composition.

2. Chemical Initiators

Examples of chemical initiators include a wide range of peroxides, other per components, and other free radical generators. A two-part chemical curing system as described more fully below, typically includes a peroxide constituent in one part and an amino compound in another. Exemplary peroxides include benzoyl peroxide, 2-butanone peroxide, lauroyl peroxide and tert-butyl peroxide. Examples of amino compounds include dimethylamino ethyl methacrylate, triethyl amine, 2-dimethylamino ethanol, diethylamino ethyl methacrylate, trihexyl amine, N,N-dimethyl-p-toluidine, N-methylethanolamine, 2,2'(p-tolyimino) diethanol, and derivatives thereof.

In an exemplary embodiment, the chemical initiator is included in the composition in an amount so as to provide sufficient time to allow the dentist or dental practitioner to have sufficient time to place the resinous sealing or filling material into the root canal. In other words, once mixed, the curing time will be sufficiently long so as to allow the dentist to carry out a desired sealing and/or filling procedure.

In most cases, it will be advantageous to include a chemical curing agent (i.e. initiator) in order for the polymerizable resin to cure within a time period of about 5 minutes to about 2 hours, more preferably from about 10 minutes to about one hour and even more preferably from about 10 minutes to about 20 minutes. Such time periods generally provide sufficient time to determine whether or not the sealing material has been properly placed.

Chemical initiators are preferably included in an amount in a range from about 0.01% to about 5% by weight of the composition, more preferably in a range from about 0.05% to about 2% by weight, and most preferably in a range from about 0.1% to about 1% by weight of the composition.

C. Curing

The compositions within the scope of the invention can be chemically curable, photo curable, or dual curable. In the case of chemical and dual curable sealing or filling compositions it is typically necessary to provide a two-part (or multi-part) composition that is mixed by the dentist just prior to use. One part includes constituents of the resin sealing or filling together with one-half of the chemical cure system (e.g., a peroxide compound), while another part includes constituents of the resin sealing with the other half of the chemical cure system (e.g., an amino compound). In the case of a photocurable sealing or filling composition, the polymerizable resin is advantageously stable in the presence of the photoinitiator absent the application of radiant energy.

In the case of chemically curable systems, the final endodontic sealing or filling composition, upon mixing the multiple parts together, preferably cures within a time period of about 15 minutes.

In the case of a photocurable system, including dual cure systems, irradiating the sealing or filling composition with radiant energy, such as from an ultraviolet curing lamp, can effect much more rapid curing than chemical cure (or chemical cure alone). The upper 1–3 mm of sealing or filling material within the root canal or dental preparation is typically photocured in a period of time of about 10 seconds to about one minute. As discussed more fully below, curing is coordinated with gas releasing to form a sealing or filling composition with minimal or no shrinkage.

II. Gas Releasing Component

In an exemplary embodiment, the gas releasing component is a compound or mixture of compounds that can react or decompose to form an inert gas such as $CO_2$ or $N_2$. As discussed more fully below, the production of gas can be designed to offset polymerization shrinkage.

A. Acid-Base Reactions

According to one embodiment, an acid and a base are included in the sealer and filler composition and react to produce a gas such as $CO_2$. Examples of acids suitable for use in the present invention include methacrylic acid, citric acid, acetic acid, maleic acid, unsaturated organic acids, and other biocompatible acids. Suitable bases that can be used in the present invention include carbonates, bicarbonates and the like.

The acid and base are selected such that the reaction of the acid and base evolves a gas. For example, when an acid is reacted with a carbonate ($CO_3^=$), the carbonate is protonated by the acid to form carbonic acid ($H_2CO_3$), which then decomposes to form $CO_2$ gas and water.

The combination of bicarbonate ($HCO_3^-$) and citric acid is particularly suitable for use in the present invention since both are commonly used in foods and would rarely, if ever, harm a patient. However, other combinations of acids and bases can be used to produce a gas even if the acids and bases have an undesirable taste or other non-harmful characteristic.

When using an acid-base reaction to produce gas, the reaction typically begins as soon as the acid and base are combined. Thus, a gas releasing component in the form of an acid and a base is usually carried out in combination with a two-part chemical curing system. In this embodiment, the gas producing acid and base are kept separate with the two parts of the curing system. Upon combining the two parts, polymerization and gas production are advantageously initiated simultaneously. Of course, if desired the acid-base gas releasing component can be used in conjunction with a single part curing system such as with a photo-initiator.

B. Other Gas Releasing Reactions and/or Decomposition

The filler and sealer composition of the present invention can include non acid-base compounds that react or decompose to form a gas. Azo-(bis)-isobutyronitrile ("AIBN") is an example of a compound that decomposes upon heating. Heating AIBN causes the molecule to decompose into $N_2$ gas and two free radicals, which quickly react with each other or another compound. An advantage of a gas-releasing compound that releases gas as a result of heat rather than chemical reaction is that it is especially useful in a one-part composition (e.g., a one-part photocurable composition).

Free radical generators such as AIBN can also be used to perform initiation of the polymerizable material, as discussed above. However, AIBN can be used with a different initiator such as benzoyl peroxide and produce a gas releasing function rather than an initiation function. In a mixture of benzoyl peroxide and AIBN, it is believed that the benzoyl peroxide is primarily the cause of initiation because it reacts more quickly with the polymerizable material.

Examples of other azo-bis compounds that can be used with the present invention include free radical sources sold by DuPont under the trademark VAZO. Suitable VAZO compounds include, VAZO 67 (butane nitrile, 2-methyl, 2,2'-azobis) and VAZO 88 (cyclohexane carbonitrile, 1,1'- azobis), VAZO 56 (2,2'-azobis(2-amidinopropane)dihydrochloride), and VAZO 68 (4,4'-azobis(4-cyanovaleric acid)).

Yet another gas producing compound suitable for use in the present invention includes isocyanate and water. Adding water to isocyanate adds a hydroxyl group to the isocyanate. The hydroxylated isocyanate then decomposes to produce $CO_2$. While isocyanate can be used to produce $CO_2$, its use in the sealing and filling compositions of the present invention can be less desirable since isocyanate can aggravate human tissue. However, the negative effects are minimized in the case of filing or sealing a root canal in a non-vital tooth.

The foregoing acid-base reactions, azo-bis compounds, isocyanate and water, and the like are examples of means for releasing a gas into a polymerizable material III. Dispersing Agent In an exemplary embodiment, the sealing and filling compositions include a a dispersing agent, such as a nucleating agent or a surfactant, to disperse gas produced by the gas releasing component. Large gas bubbles in the polymeric material can be undesirable if the bubbles create weak spots in the material or provide pathways for microbes to pass through. The dispersing agent is mixed with the sealer and filler composition such that as gas is released, the gas is dispersed within the polymerized composition as fine bubbles.

Dispersing agents suitable for use in the present invention include nucleating agents such as benzoic acid, talc, titanium oxide, fumed silica, and azodicarbonamide. Surfactants suitable for use in the present invention include sorbitan monooleate, dimethicon, and simethican (activated dimethicon with a molecular weight between 14,000 and 18,000 and mixed with silicone dioxide). In one embodiment, a silicon based surfactant such as SILWET 77, manufactured and sold by the Setre Chemical Company, is included to disperse gas bubbles. Other dispersing agents include aluminum salts such as aluminum benzoate, Inorganic agents, such as antimony trioxide, phosphate, and sodium salts, such as sodium 4-methylvalerate can be used in the present invention. Those skilled in the art will recognize that there are many dispersing agents, including other nucleating agents and surfactants that can be used to disperse gasses in the composition of the present invention. Furthermore, some dispersing agents can act as both a nucleating agent and a surfactant.

IV. Fillers and Other Additives

Fillers and additives can be included in the composition to impart desired properties. One purpose of adding a filler, such as silicon dioxide or calcium phosphate tribasic, is to reduce polymer shrinkage. Fillers do not polymerize and therefore do not experience polymerization shrinkage. Thus replacing the polymerization material with filler reduces polymerization shrinkage.

In one embodiment the filler and sealer composition includes radioopaque fillers to provide the ability of the dentist to X-ray and determine how well the endodontic resin has penetrated into and filled the root canal. Examples of fillers that can provide increased radioopacity include bismuth salts such as bismuth chloride, silver and silver salts such as silver chloride, barium salts such as barium sulfate or barium chloride, tungsten salts, titanium dioxide, and strontium salts such as strontium sulfate and strontium chloride.

It is within the scope of the invention to include fillers in an amount of up to about 85% by weight of the composition, more preferably in a range from about 2% to about 70% by weight, and most preferably in a range from about 5% to about 50% by weight of the composition.

The sealing or filling compositions of the present invention may optionally include one or more antimicrobial agents to assist in cleansing and sterilizing the root canal and to prevent later infection. Examples of suitable antibacterial agents include organohalogens, antibiotics, alkali metal hydroxides, alkaline earth metal oxides, and alkaline earth metal hydroxides.

Examples of antibacterial organohalogens include 1,1'-hexamethylene bis(5(p-chlorophenyl)biguanide), cetyl pyridinium chloride, benzalkonium chloride, and cetyl pyridinium bromide.

Examples of suitable antibiotics include: 4'-sulfamoylsulfanilanilide, 3-amino-6-(2-(5-nitro-2-furyl)vinyl)pyridazine, trans-pseudomonic acid, xanthomycin, alpha-amino-p-toluene sulfonamide, alpha-azido benzyl penicillin, penicillin O, penicillin N, monopropionyl erthromycin, and erythromycin 9(O-((2-methoxy ethoxy)methyl)

Examples of suitable alkali metal hydroxides include sodium hydroxide and lithium hydroxide. Examples of suitable alkaline earth metal oxides include calcium oxide, magnesium oxide, barium oxide, and strontium oxide. Examples of suitable alkaline earth metal hydroxides include calcium hydroxide, magnesium hydroxide, barium hydroxide, and strontium hydroxide.

In one embodiment, the composition includes calcium hydroxide since calcium hydroxide not only kills microorganisms but is chemically compatible with dental tissue. The antimicrobial agent may be included in an amount in a range from about 0.001% to about 30% by weight of the composition, preferably in a range from about 0.005% to about 10% by weight, and most preferably in a range from about 0.01% to about 5% by weight of the composition.

It is also within the scope of the invention to include other additives or adjuvents, such as solvents, dyes, or plasticizers, to impart desired properties. For example, silica may be included in order to impart hardness. Keeping the silica content low, however, improves the ability to later drill out a portion of the cured material if desired, such as to place a post during a crown restoration.

V. Controlling Shrinkage

Polymerization shrinkage is primarily controlled or offset by selecting proper amounts of gas releasing component. The proper amount of gas releasing component is proportional to the amount of polymerizable material in the composition. Increasing the percentage of polymerizable material generally requires an increase in gas releasing component. A particular ratio of polymerizable material to gas releasing component produces a desired net shrinkage.

The proper ratio of polymerizable material to gas releasing component can depend on the type of polymerizable material. Typically polymerizable materials shrink about 12% to 16% upon polymerization. Polymerization shrinkage is a property of the polymerizable material and thus is generally predictable for a given amount of a specific polymerizable material.

Since the polymerizable material is only one part of the overall composition, the composition may experience less shrinkage than the polymerizable material alone. The sealing and filling composition of the present invention typically experiences shrinkage between about 5% and 12%, absent the gas releasing component. Of course the invention includes polymerizable materials and compositions that experience more or less shrinkage in the absence of the gas releasing component.

The amount of gas releasing component is selected to give the composition a desired net shrinkage. Shrinkage can be either negative or positive. A negative shrinkage indicates expansion. In an exemplary embodiment, the amount of gas releasing component is selected and included in the composition to provide between about 6% and about −6% net shrinkage, more preferably between about 3% and about −3% net shrinkage, even more preferably between about 1% and about −1% shrinkage, and most preferably substantially 0.0% net shrinkage (in the overall composition). A composition that experiences little or no shrinkage can have superior bonding characteristics because the material does not pull away from the tissue as it hardens. Little or no shrinkage also minimizes the risk that the composition will break a tooth or cause other damage due to expansion.

Despite the foregoing, the present invention contemplates forming compositions that experience significant shrinkage or even negative shrinkage (i.e. expansion). Shrinkage or expansion in some cases can be desirable. For example, expansion in a root canal can cause the composition to be forced into the tubules of the root canal. Those skilled in the art will recognize that the advantage of the present invention, among others, is that a user can control the amount of shrinkage whether it be negative, positive, or near or at zero. The present invention, rather than limiting the composition to a particular type or amount of polymerizable material, as do the composition in the prior art, allows the user to control the shrinkage using the gas releasing component.

Those skilled in the art will recognize that there are numerous combinations of polymerizable materials and gas releasing components that can be combined to produce a composition with almost any desired amount of net shrinkage. To offset polymerization shrinkage to within a range of about 1% net shrinkage, an acid-base gas releasing component can be included in the composition. The acid-base gas releasing component includes acid in a range of about 0.1% to about 2% and base in an amount of about 0.1% to about 2% of base and water in an amount of about 0.25% to about 2%.

In an exemplary embodiment, the base and water are the limiting reagents in an acid-base reaction. Water provides an aqueous environment for the acid-base reaction to occur. Thus, increasing the amount of water, up to 2% or more for example, increases the production of gas where water is a limiting reagent (percentages are based on the amount in a single part of a two part system). Furthermore, the composition's ability to absorb water can depend on the existence and or amount of a hydrophilic resin. Exemplary hydrophilic resins suitable for use in the present invention includes glycerol dimethacrylate phosphate, bis-glycerol dimethacrylate phosphate, and 2-hydroxy ethylmethacrylate phosphate.

Composition according to the present invention that include an azo-bis compound, such as VAZO 88, control shrinkage by evolving nitrogen gas. The VAZO compound is included in an amount of about 0.5% to about 2%.

Other components in the sealer or filler composition can affect the amount of gas releasing component needed to create a desired net shrinkage. For example, the amount of filler in the composition can affect the amount of polymerizable material in the composition, thereby affecting the amount of gas releasing component required to offset polymerization shrinkage. Generally, increasing the amount of filler reduces the amount of polymerizable material used in the composition and reduces the amount of gas releasing component needed to produce the desired net shrinkage.

Factors other than the amount of gas releasing component can be important to achieve proper expansion for offsetting polymerization shrinkage. One factor includes designing the composition to produce gas simultaneously with polymerization. If gas production occurs too fast, then the gas dissipates before the sealer and filler composition can sufficiently stiffen or harden. If gas production is too slow, the gas releasing component will not create the desired expansion before the composition cures. Once the composition is cured, gas production has little or no effect on expansion.

The rate of polymerization, and thus the working time available before the composition hardens, depends in large part on the percentage of initiator. Increasing the amount of initiator increases the rate of polymerization and thus reduces the working time. For example, benzoyl peroxide and tolyimino diethanol can be included in concentrations of about 0.1% to about 0.5% (in one part of a two part system) to provide a working time of about 10 minutes to 15 minutes and a setting time of about 15 minutes to about 35 minutes.

The rate of polymerization, and thus working time, can depend on constituents other than the initiator. For example, acids used in an acid-base gas producing reaction can stabilize peroxides such as benzoyl peroxide. Stabilizing a peroxide initiator decreases the rate of polymerization and increases the working time. However, the amount of initiator can be increased to offset this stabilizing effect.

Examples of the present invention are presented herein as illustrative of some embodiments of the present invention. These examples are not to be construed as limiting the scope of the invention. Examples written in past tense refer to actual compositions that have been made, while those in present tense are hypothetical in nature, though based on mix designs that have already been made.

EXAMPLE 1

A dual cure dental composition suitable as a sealing or filling material was prepared in two parts and included an acid-base gas releasing component. Each part had the following components in the stated amount:

| Part 1 | |
|---|---|
| Citric Acid | 1.2% |
| Deionized Water | 2.0% |
| Triethylene Glycol Dimethacrylate | 3.6% |
| Benzoyl Peroxide | 1.2% |
| Diurethane Dimethacrylate | 25.0% |
| Glycerol Dimethacrylate Phosphate | 10.0% |
| Bismuth Oxide Chloride | 40.0% |
| Calcium Lactate Pentahydrate | 6.0% |
| Silicon Dioxide | 2.0% |
| Total Part 1: | 100.0% |
| Part 2 | |
| Sodium Bicarbonate | 1.0% |
| Triethylene Glycol Dimethacrylate | 15.8% |
| P-Tolyimino Diethanol | 0.2% |
| Diurethane Dimethacrylate | 35.0% |
| Bismuth Oxide Chloride | 40.0% |
| Calcium Lactate Pentahydrate | 6.0% |
| Silicon Dioxide | 2.0% |
| Total Part 2 | 100.0% |
| Net Shrinkage | 6.8% |

EXAMPLE 2

A dual cure dental composition suitable as a sealing or filling material was prepared in two parts and included an acid-base gas releasing component. Each part had the following components in the stated amount:

| Part 1 | |
|---|---|
| Triethylene Glycol Dimethacrylate | 16.0% |
| Diurethane Dimethacrylate | 27.7% |
| Glycerol Dimethacrylate Phosphate | 10.0% |
| Bismuth Oxide Chloride | 40.0% |
| Aerosil200 | 2.0% |
| Benzoyl Peroxide | 0.3% |
| Citric Acid | 1.0% |
| Water | 2.0% |
| Silicone Surfactant (SILWET) | 1.0% |
| Total Part 1 | 100.0% |
| Part 2 | |
| Triethylene Glycol Dimethacrylate | 16.8% |
| Diurethane Dimethacrylate | 30.0% |
| Bismuth Oxide Chloride | 50.0% |
| Aerosil200 | 2.1% |
| P-Tolyimino Diethanol | 0.3% |
| Sodium Bicarbonate | 0.8% |
| Total Part 2 | 100.0% |
| Net Shrinkage | −6.8% |

EXAMPLE 3

A dual cure dental composition suitable as a sealing or filling material was prepared in two parts and included an acid-base gas releasing component. Each part had the following components in the stated amount:

| Part 1 | |
|---|---|
| Triethylene Glycol Dimethacrylate | 15.8% |
| Diurethane Dimethacrylate | 30.3% |
| Glycerol Dimethacrylate Phosphate | 10.0% |
| Bismuth Oxide Chloride | 37.0% |
| Calcium Lactate | 2.0% |
| Aerosil 200 | 2.0% |
| Benzoyl Peroxide | 0.2% |
| Citric Acid | 1.45% |
| Water | 1.25% |
| Silicone Surfactant (SILWET) | 1.25% |
| Total Part 1 | 100.0% |
| Part 2 | |
| Triethylene Glycol Dimethacrylate | 16.8% |
| Diurethane Dimethacrylate | 39.8% |
| Bismuth Oxide Chloride | 33.0% |
| Aerosil200 | 3.0% |
| Calcium Lactate | 6.0% |
| P-Tolyimino Diethanol | 0.2% |
| Sodium Bicarbonate | 1.2% |
| Total Part 2 | 100.0% |
| Net Shrinkage | 1.25% |

EXAMPLE 4

A dual cure dental composition suitable as a sealing or filling material was prepared in two parts and include a VAZO based gas-releasing component. Each part had the following components in the stated amount:

| Part 1 | |
|---|---|
| Triethylene Glycol Dimethacrylate | 16.8% |
| TIDE | 0.2% |
| Diurethane Dimethacrylate | 35.0% |
| Bismuth Oxide Chloride | 40.0% |
| Calcium Lactate Pentahydrate | 6.0% |
| Silicon Dioxide | 2.0% |
| Total Part 1 | 100.0% |
| Part 2 | |
| VAZO 88 | 1.0% |
| Triethylene Glycol Dimethacrylate | 14.8% |
| Benzoyl Peroxide | 0.2% |
| Diurethane Dimethacrylate | 26.0% |
| Glycerol Dimethacrylate Phosphate | 10.0% |
| Bismuth Oxide Chloride | 40.0% |
| Calcium Lactate Pentahydrate | 6.0% |
| Silicon Dioxide | 2.0% |
| Total Part 2 | 100.0% |
| Net Shrinkage | −6.4% |

EXAMPLE 5

A dual cure dental composition suitable as a sealing or filling material was prepared in two parts and included a VAZO based gas-releasing component. Each part had the following components in the stated amount:

| Part 1 | |
|---|---|
| Triethylene Glycol Dimethacrylate | 16.8% |
| Diurethane Dimethacrylate | 30.0% |
| Glycerol Dimethacrylate Phosphate | 5.0% |
| Bismuth Oxide Chloride | 40.0% |
| Calcium Lactate | 6.0% |
| Aerosil200 | 2.0% |
| Benzoyl Peroxide | .20% |
| Total Part 1 | 100.0% |
| Part 2 | |
| Triethylene Glycol Dimethacrylate | 15.8% |
| Diurethane Dimethacrylate | 30.0% |
| Glycerol Dimethacrylate Phosphate | 5.0% |
| Bismuth Oxide Chloride | 40.0% |
| Calcium Lactate | 6.0% |
| Aerosil200 | 2.0% |
| P-Tolyimino Diethanol | 0.2% |
| VAZO 88 | 1.0% |
| Total Part 2 | 100.0% |
| Net Shrinkage | 6.4% |

EXAMPLE 6

A dual cure dental composition suitable as a sealing or filling material was prepared in two parts and included a VAZO based gas-releasing component. Each part had the following components in the stated amount:

| Part 1 | |
|---|---|
| Triethylene Glycol Dimethacrylate | 16.8% |
| Diurethane Dimethacrylate | 30.0% |
| Glycerol Dimethacrylate Phosphate | 5.0% |
| Bismuth Oxide Chloride | 40.0% |
| Calcium Lactate | 6.0% |
| Aerosil200 | 2.0% |
| Benzoyl Peroxide | .20% |
| Total Part 1 | 100.0% |
| Part 2 | |
| Triethylene Glycol Dimethacrylate | 15.8% |
| Diurethane Dimethacrylate | 30.5% |
| Glycerol Dimethacrylate Phosphate | 5.0% |
| Bismuth Oxide Chloride | 40.0% |
| Calcium Lactate | 6.0% |
| Aerosil200 | 2.0% |
| P-Tolyimino Diethanol | 0.2% |
| VAZO 88 | .50% |
| Total Part 2 | 100.0% |
| Net Shrinkage | 2.9% |

As discussed above, the present invention is typically used during root canal procedures or other dental procedures where sealing tissue and/or filling a cavity is required. Those skilled in the art are familiar with using sealer and filler compositions to perform such tasks. Those skilled in the art will also recognize that by controlling shrinkage, the sealer and filler compositions of the present inventions can be used to perform additional procedures where polymerization shrinkage has previously prevented such use.

The present invention can be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A one- or multi-part composition for filling or sealing a void comprising:
   a polymerizable material that undergoes polymerization shrinkage of about 12% to about 16% upon polymerization;
   a polymerization initiator; and
   a gas releasing component in addition to the polymerization initiator that, when mixed with the polymerizable material, is configured to release a gas therein during polymerization of the polymerizable material, the gas causing the composition to expand to at least partially offset the polymerization shrinkage of the polymerizable material,
   wherein the gas releasing component is included in an amount so that the composition has a net shrinkage between about 6% and about −6% after polymerization of the polymerizable material.

2. A composition as in claim 1, further comprising a dispersing agent that disperses the gas in the composition as it is released.

3. A composition as in claim 2, wherein the dispersing agent is selected from the group consisting of benzoic acid, talc, titanium oxide, fumed silica, and azodicarbonamide, sorbitan monooleate, dimethicon, and simethican.

4. A composition as in claim 1, wherein the gas releasing component comprises an acid and a base, wherein the composition further comprises water.

5. A composition as in claim 4, wherein the acid is selected from the group consisting of methacrylic acid, citric acid, maleic acid, acetic acid, and combinations thereof.

6. A composition as in claim 4, wherein the base is selected from the group consisting of carbonate, bicarbonate, and combinations thereof.

7. A composition as in claim 4, wherein the base comprises bicarbonate and the acid comprises citric acid.

8. A composition as in claim 1, wherein the gas releasing component is an azo-bis compound.

9. A composition as in claim 8, wherein the azo-bis compound is azo-(bis)isobutyronitrile.

10. A composition as in claim 1, wherein the gas releasing component comprises water and an isocyanate.

11. A composition as in claim 1, wherein the gas released is an inert gas.

12. A composition as in claim 11, wherein the gas released is selected from the group consisting of carbon dioxide, nitrogen, and combinations thereof.

13. A composition as in claim 1, wherein the polymerization initiator is selected from the group consisting of a chemical initiator, a photoinitiator, and combinations thereof.

14. A composition as in claim 1, wherein the gas releasing component is included in an amount so that the net shrinkage of the composition is between about 3% and about −3%.

15. A composition as in claim 1, wherein the gas releasing component is included in an amount so that the net shrinkage of the composition is between about 1% and about −1%.

16. A multi-part composition for filling or sealing a void comprising:
   a polymerizable material that is at least partially hydrophilic and undergoes polymerization shrinkage upon polymerization;
   a chemical initiator capable of initiating polymerization of the polymerizable material when mixed therewith;
   water; and
   a gas releasing component comprising an acid and a base that are initially separated from each other, wherein upon mixing of the multi-part composition, the acid and the base react to release a gas that causes the composition to expand to at least partially counteract the polymerization shrinkage of the polymerizable material.

17. A composition as in claim 16, wherein the base is selected from the group consisting of a carbonate, bicarbonate, and combinations thereof.

18. A composition as in claim 16, wherein the acid is selected from the group consisting of citric acid, acetic acid, maleic acid, and combinations thereof.

19. A composition as in claim 16, wherein the initiator is included in an amount that causes the mixed composition to harden within about 5 minutes to about an hour from mixing.

20. A method according to claim 16, wherein the initiator is included in an amount that causes the mixed composition to harden within about 10 minutes to about 30 minutes from mixing.

21. A method according to claim 16, wherein the initiator is included in an amount that causes the mixed composition to harden within about 10 minutes to about 20 minutes from mixing.

22. A one- or multi-part composition for filling or sealing a void comprising:
- a polymerizable material that undergoes polymerization shrinkage upon polymerization;
- a polymerization initiator; and
- means, in addition to the polmerization initiator, for releasing a gas into the polymerizable material during polymerization thereof, the means for releasing a gas causing a volume of the composition to expand to at least partially counteract the polymerization shrinkage of the polymerizable material,
- wherein the composition has a net shrinkage between about 5% and 12% in the absence of the means for releasing a gas,
- wherein the means for releasing a gas are included in an amount in order for the composition to have a net shrinkage between about 3% and about −3%.

23. A composition as in claim 22, wherein the means for releasing a gas comprise an acid and a base that react to form carbon dioxide.

24. A composition as in claim 22, wherein the means for releasing a gas comprise an azo-bis compound.

25. A method for treating a tooth following a dental procedure comprising:
- providing a tooth having a dental preparation formed therein;
- introducing a filling and sealing composition into the dental preparation, the composition being comprised of a polymerizable material, a polymerization initiator, and a gas releasing component in addition to the polymerization initiator; and
- causing or allowing the filling and sealing composition to cure in a manner so that the composition releases gas internally in order to at least partially offset polymerization shrinkage.

26. A method for treating a tooth following a dental procedure comprising:
- providing a tooth having a dental preparation formed therein;
- introducing a filling and sealing composition into the dental preparation, the composition being comprised of a polymerizable material, water, an acid, and a base that releases carbon dioxide gas when reacted with the acid; and
- causing or allowing the filling and sealing composition to cure in a manner so that the composition releases carbon dioxide gas internally in order to at least partially offset polymerization shrinkage.

* * * * *

UNITED STATES PATENT AND TRADEMARK OFFICE
CERTIFICATE OF CORRECTION

PATENT NO. : 7,173,075 B2  Page 1 of 1
APPLICATION NO. : 10/929296
DATED : February 6, 2007
INVENTOR(S) : Wagner et al.

It is certified that error appears in the above-identified patent and that said Letters Patent is hereby corrected as shown below:

Column 2
Line 63, after "material" insert --to--

Column 3
Line 15, change "had" to --hand--
Line 55, change "select" to --selected--

Column 4
Line 39, change "import" to --important--
Line 47, change "monomer" to --monomers--

Column 8
Line 17, after "methyl)" add --oxime.--
Line 42, change "component" to --components--

Signed and Sealed this

Twenty-second Day of July, 2008

JON W. DUDAS
*Director of the United States Patent and Trademark Office*